United States Patent
Doering

(10) Patent No.: US 10,238,594 B2
(45) Date of Patent: Mar. 26, 2019

(54) ANTIPERSPIRANTS HAVING INCREASED EFFECTIVENESS

(71) Applicant: Henkel AG & Co. KGaA, Duesseldorf (DE)

(72) Inventor: Thomas Doering, Dormagen (DE)

(73) Assignee: Kenkel AG & Co. KGaA, Duesseldorf (DE)

( * ) Notice: Subject to any disclaimer, the term of this patent is extended or adjusted under 35 U.S.C. 154(b) by 37 days.

(21) Appl. No.: 15/545,726

(22) PCT Filed: Nov. 12, 2015

(86) PCT No.: PCT/EP2015/076448
§ 371 (c)(1),
(2) Date: Jul. 24, 2017

(87) PCT Pub. No.: WO2016/119937
PCT Pub. Date: Aug. 4, 2016

(65) Prior Publication Data
US 2018/0000708 A1    Jan. 4, 2018

(30) Foreign Application Priority Data

Jan. 30, 2015 (DE) .................. 10 2015 201 653

(51) Int. Cl.
| | | |
|---|---|---|
| *A61K 8/04* | (2006.01) | |
| *A61K 8/06* | (2006.01) | |
| *A61K 8/26* | (2006.01) | |
| *A61K 8/28* | (2006.01) | |
| *A61K 8/368* | (2006.01) | |
| *A61K 8/44* | (2006.01) | |
| *A61K 8/365* | (2006.01) | |
| *A61Q 15/00* | (2006.01) | |

(52) U.S. Cl.
CPC .............. *A61K 8/44* (2013.01); *A61K 8/042* (2013.01); *A61K 8/046* (2013.01); *A61K 8/06* (2013.01); *A61K 8/26* (2013.01); *A61K 8/28* (2013.01); *A61K 8/365* (2013.01); *A61K 8/368* (2013.01); *A61Q 15/00* (2013.01); *A61K 2800/874* (2013.01)

(58) Field of Classification Search
CPC .......... A61K 8/44; A61K 8/042; A61K 8/046; A61K 8/26; A61K 8/06; A61K 8/28; A61K 8/368; A61K 2800/874; A61Q 15/00

See application file for complete search history.

(56) References Cited

FOREIGN PATENT DOCUMENTS

| WO | 2006/056283 A1 | 6/2006 |
|---|---|---|
| WO | 2013174725 A2 | 11/2013 |

OTHER PUBLICATIONS

EPO, International Search Report and Written Opinion issued in International Application No. PCT/EP2015/076448, dated Dec. 16, 2015.

*Primary Examiner* — Alma Pipic
(74) *Attorney, Agent, or Firm* — Lorenz & Kopf, LLP

(57) ABSTRACT

The present disclosure relates to antiperspirant cosmetic agents, in the case of which the total amount of antiperspirant compounds can be clearly reduced without the antiperspirant effect of said agents or the storage stability of said agents being impaired, comprising—in each case with respect to the total weight of the antiperspirant cosmetic agent—a) 1 to 30 wt % of at least one antiperspirant compound, b) 0.1 to 10 wt % of salicylic acid, c) at least one compound of formula (I), in which n represents 0 or 1, X represents —H, Na+, K+, or NH4+, R1 is selected from —H, —COOX, or —(CH2)—COOX, R2 is selected from —H, C1-10 alkyl, or COOX, R3 is selected from —(CH2)—COOX, —(CH2)2-N[(CH2)—COOX]2, —CH(R1)—COOX, —(CH2)2-NH[CH(COOX)(CH2COOX)], —CH(R4)—C(R5)(R6)—COOX, R4 is selected from —H, C1-10 alkyl, or COOX, and R5 and R6 are, independently of each other, —H, —OH, or C1-10 alkyl.

19 Claims, No Drawings

ANTIPERSPIRANTS HAVING INCREASED EFFECTIVENESS

CROSS-REFERENCE TO RELATED APPLICATION

This application is a U.S. National Stage entry under 35 U.S.C. § 371 based on International Application No. PCT/EP2015/076448, filed Nov. 12, 2015 which was published under PCT Article 21(2) and which claims priority to German Application No. 102015201653.6 filed Jan. 30, 2015, which are all hereby incorporated in their entirety by reference.

TECHNICAL FIELD

The present disclosure pertains to an antiperspirant cosmetic composition comprising at least one antiperspirant compound, optionally at least one propellant, and other special compounds. The addition of these other compounds allows the quantity of the antiperspirant compound to be reduced without impairing the antiperspirant effect of the cosmetic agent.

The present disclosure further relates to a packaging unit (kit-of-parts) comprising a cosmetic composition as contemplated herein and a cosmetic composition comprising at least one antiperspirant compound.

The present disclosure also relates to the use of a combination comprising at least one antiperspirant compound, optionally at least one propellant and other special compounds to reduce and/or prevent perspiration, particularly underarm perspiration or perspiration from other parts of the body.

Finally, the present disclosure relates to a non-therapeutic cosmetic method for preventing and/or reducing body perspiration in which an antiperspirant cosmetic composition as contemplated herein or the content of a packaging unit as contemplated herein is applied to the skin, in particular on the skin of armpits and remains in contact with the underarm skin for at least about 1 hour, preferably at least about 2 hours, more preferably at least about 4 hours, particularly at least 6 hours.

BACKGROUND

Washing, cleaning and caring for one's body is a basic human need, and modern industry is constantly trying to meet these needs of the individual in many ways. Especially important for daily hygiene is the regular elimination or at least reduction of body odour and underarm wetness. Many specific deodorant or antiperspirant body care products are known from the prior art, having been developed for use in areas of the body with a high density of sweat glands, especially in the underarm area. They are packaged in a wide variety of administration forms, for example as powders, in stick form, as aerosol sprays, pump sprays, liquid and gel roll-on applications, lotions, gels and impregnated flexible substrates (deodorant wipes).

Besides at least one oil or wax and a fragrance component or perfume, cosmetic antiperspirants of the prior art contain at least one antiperspirant compound, particularly in the form of halides and/or hydroxyhalides of aluminium and/or zirconium. These antiperspirant compounds reduce the secretion of sweat by the body by temporarily constricting and/or obstructing the sweat gland excretory ducts, so that the quantity of sweat secreted can be reduced by about 20 to about 60 percent. At the same time, they also have a deodorising effect because of their antimicrobial function.

Halides and/or hydroxyhalides of aluminium and/or zirconium may cause unpleasant skin reactions in some users due to the acidic pH of these antiperspirants. Moreover, use of the aforementioned antiperspirant compounds can cause staining on clothing.

Accordingly, there is a need to reduce the overall quantity of antiperspirant halides and/or hydroxyhalides of aluminium and/or zirconium in the antiperspirant cosmetic products. These antiperspirant cosmetic products should have a good antiperspirant effect, they should be well tolerated on the skin and should also have good storage stability.

BRIEF SUMMARY

Antiperspirant cosmetic compositions and non-therapeutic cosmetic method for preventing and/or reducing body perspiration using such antiperspirant cosmetic compositions are provided herein. In an exemplary embodiment, an antiperspirant cosmetic composition includes, relative to the total weight of the antiperspirant cosmetic composition,
a) from about 1 to about 30 wt % of at least one antiperspirant compound,
b) from about 0.1 to about 10 wt % salicylic acid, and
c) at least one compound with formula (I)

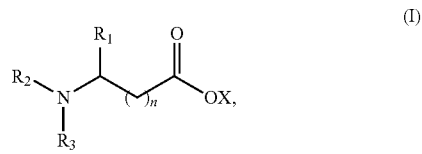

in which
n stands for 0 or 1,
X stands for —H, $Na^+$, $K^+$ or $NH_4^+$,
$R_1$ is selected from —H, —COOX or —($CH_2$)—COOX,
$R_2$ is selected from —H, $C_{1-10}$-alkyl or COOX,
$R_3$ is selected from —($CH_2$)—COOX, —($CH_2$)$_2$—N[($CH_2$)—COOX]$_2$, —CH($R_1$)—COOX, —($CH_2$)$_2$—NH[CH(COOX)($CH_2$COOX)], —CH($R_4$)—C($R_5$)($R_6$)—COOX,
$R_4$ is selected from —H, $C_{1-10}$-alkyl or COOX, and
$R_5$, $R_6$ are independently —H, —OH or $C_{1-10}$-alkyl.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object underlying the present disclosure was to provide an antiperspirant cosmetic composition which avoids or at least mitigates the disadvantages of the prior art, and which is well tolerated by the skin while still assuring reliable reduction of underarm wetness. The antiperspirant cosmetic products should also have a long shelf life.

Surprisingly, it has been found that the total quantity of antiperspirant compounds may be reduced significantly without adversely affecting the antiperspirant action or the storage stability of said compounds when salicylic acid and specific nitrogen-containing compounds are used in cosmetic compositions.

The object of the present disclosure is thus an antiperspirant cosmetic composition comprising—in each case relative to the total weight of the antiperspirant cosmetic composition
a) from about 1 to about 30 wt % of at least one antiperspirant compound,
b) from about 0.1 to about 10 wt % salicylic acid
c) at least one compound with formula (I)

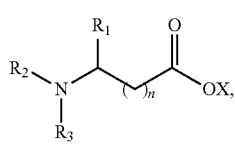

in which
n stands for 0 or 1,
X stands for —H, Na+, K+ or NH4+,
$R_1$ is selected from —H, —COOX or —(CH$_2$)—COOX,
$R_2$ is selected from —H, C$_{1-10}$-alkyl or COOX,
$R_3$ is selected from —(CH$_2$)—COOX, —(CH$_2$)$_2$—N[(CH$_2$)—COOX]$_2$, —CH(R$_1$)—COOX, —(CH$_2$)$_2$—NH[CH(COOX)(CH$_2$COOX)], —CH(R$_4$)—C(R$_5$)(R$_6$)—COOX
$R_4$ is selected from —H, C$_{1-10}$-alkyl or COOX,
$R_5$, $R_6$ are independently —H, —OH or C$_{1-10}$-alkyl.

The compositions as contemplated herein comprise from about 1 to about 30 wt %/o of at least one antiperspirant compound. The antiperspirant compounds particularly preferably comprise aluminium chlorohydrate or aluminium zirconium chlorohydrate. These compounds are prepared in aqueous solution by hydrolysis of Al(all) and Zr(IV) aqua complexes in a pH range from about 4 to about 7. In both cases, oligomeric and polymeric complexes form with hydroxide and oxide bridges between the metal ions. In high concentrations, there is a strong tendency to form high molecular weight complexes (about 2000-about 10000 Da). In these cases, the antiperspirant effectiveness is only very weak. Smaller complex cations (about 500-about 1500 Da), the monomer AlC$_3$×6 H2O and the dimer Al$_2$(OH)$_2$(H2O)$_4$+ are significantly more effective. In dilute aqueous solutions, the equilibrium can be shifted towards the small polymers, but then the overall concentration is no longer sufficient to achieve an adequate antiperspirant effect.

When aqueous solutions of aluminium chloride are not neutralised, practically no hydrolysis takes place, and Al(H$_2$O)$_6$Cl$_3$ remains largely in the monomeric configuration. Such solutions exhibit pronounced antiperspirant effectiveness and are used among other things for prescription antiperspirants to treat hyperhidrosis. However, these solutions are very poorly tolerable to the skin and they are not suitable for use in cosmetic products.

The antiperspirant effectiveness of concentrated solutions of aluminium chlorohydrate or aluminium zirconium chlorohydrate may be increased significantly by adding salicylic acid and compound(s) of formula (I). Without wishing to be bound by theory, the applicant supposes that the combination of salicylic acid and compound(s) of formula (I) is able to stabilise small complex cations so that aggregation into high molecular weight complexes is limited. This creates a highly effective aqueous formulation with excellent skin tolerability without the need to add aluminium chloride.

For the purpose of the present disclosure, the term "antiperspirant" is understood to relate to the reduction or limitation of transpiration from the body's sweat glands.

Similarly, in the context of the present disclosure the term "antiperspirant compound" is understood to refer to halides and/or hydroxyhalides of aluminium and/or zirconium, particularly chlorides, bromides and iodides of aluminium and zirconium, as well as compounds with formulas Al(OH)$_2$X and Zr(OH)$_2$X, wherein X stands for a halide ion in the aforementioned formulas. The same term is further understood to include complexes of halides and/or hydroxyhalides of aluminium and/or zirconium with ligands, such as amino acids, betaines and hydroxyalkanoic acids.

The antiperspirant cosmetic compositions as contemplated herein comprise at least one antiperspirant compound in a total quantity of about 1 to about 30 wt % relative to the total weight of the cosmetic composition as component a).

Within the scope of the present disclosure, the antiperspirant compound may be selected from the group of (i) water-soluble astringent inorganic salts of aluminium, particularly aluminium chlorohydrate, aluminium sesquichlorohydrate, aluminium dichlorohydrate, aluminium hydroxide, potassium aluminium sulphate, aluminium bromohydrate, aluminium chloride, aluminium sulphate, (ii) water-soluble astringent organic salts of aluminium, particularly aluminium chlorohydrex propylene glycol, aluminium chlorohydrex polyethylene glycol, aluminium propylene glycol complexes, aluminium sesquichlorohydrex propylene glycol, aluminium sesquichlorohydrex polyethylene glycol, aluminium propylene glycol dichlorohydrex, aluminium polyethylene glycol dichlorohydrex, aluminium undecylenoyl collagen amino acid, sodium aluminium lactate, sodium aluminium chlorohydroxy lactate, aluminium lipoaminoacids, aluminium lactate, aluminium chlorohydroxy allantoinate, sodium aluminium chlorohydroxy lactate; (iii) water-soluble astringent inorganic aluminium-zirconium salts, particularly aluminium-zirconium trichlorohydrate, aluminium-zirconium tetrachlorohydrate, aluminium-zirconium pentachlorohydrate, aluminium-zirconium octachlorohydrate; (iv) water-soluble astringent organic aluminium-zirconium salts, particularly aluminium-zirconium propylene glycol complexes, aluminium-zirconium trichlorohydrex glycine, aluminium-zirconium tetrachlorohydrex glycine, aluminium-zirconium pentachlorohydrex glycine, aluminium-zirconium octachlorohydrex glycine; and (v) mixtures thereof.

Particularly preferred antiperspirant cosmetic compositions as contemplated herein are exemplified in that they comprise from about 2 to about 25 wt %, preferably from about 3 to about 24 wt %, more preferably from about 4 to about 23 wt %, still more preferably from about 5 to about 20 wt %, yet more preferably from about 6 to about 19 wt % and particularly from about 8 to about 18 wt % aluminium chlorohydrate.

Further preferred compositions may also comprise aluminium zirconium salts in addition to or instead of aluminium chlorohydrate. Particularly preferred antiperspirant cosmetic compositions of such kind are exemplified in that they comprise from about 2.5 to about 29 wt %, preferably from about 5 to about 28 wt %, more preferably from about 7.5 to about 27 wt %, still more preferably from about 10 to about 26 wt %, yet more preferably from about 12.5 to about 25 wt % and especially from about 15 to about 23 wt % aluminium zirconium chlorohydrate.

For the purposes of the present disclosure, the term "antiperspirant aluminium salts" is understood not to include aluminosilicates or zeolites. Further as contemplated herein, water-soluble aluminium salts are understood to be those salts with solubility of at least about 3 wt % at 20° C., that is to say at about 3 g of the antiperspirant aluminium salt dissolves in 97 g water at 20° C.

Particularly good antiperspirant effect is obtained in the scope of the present disclosure when a total quantity from about 2 to about 20 wt %, preferably from about 2.5 to about 18 wt %, more preferably from about 3 to about 15 wt %, still more preferably from about 3.5 to about 12 wt %, yet more preferably from about 4 to about 10 wt %, particularly from about 4.5 to about 8 wt % of the antiperspirant compound(s) relative to the total weight of the antiperspirant cosmetic product is included.

According to one embodiment of the present disclosure, it may be provided that a blowing agent is used in the antiperspirant cosmetic agents as contemplated herein. If the cosmetic compositions of the present disclosure comprise a blowing agent, it is preferably present in a total amount from about 1 to about 98 wt %, preferably from about 20 to about 90 wt %, more preferably from about 30 to about 85 wt %, particularly from about 40 to about 75 wt % relative to the total weight of the antiperspirant cosmetic composition. In this case, the cosmetic compositions as contemplated herein are formulated as a propellant-driven aerosols. Preferred propellants (propellant gases) are propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluorooethane, tetrafluoropropene both individually and in mixtures thereof. Hydrophilic propellants gases such as carbon dioxide may also be used advantageously for the purposes of the present disclosure if the proportion of hydrophilic gases is selected to be low and a lipophilic propellant gas (e.g., propane/butane) is present in excess. Particularly preferred are propane, n-butane, isobutane and mixtures thereof. It has been found that the use of n-butane as the only propellant may be particularly preferred for the purposes of the present disclosure.

As a second essential ingredient, the compositions as contemplated herein comprise salicylic acid in quantities from about 0.1 to about 10 wt %, relative to the finished agents in each case—without any possibly existing propellant. It is particularly preferred to use salicylic acid within relatively narrow quantitative ranges, so preferred antiperspirant cosmetic products as contemplated herein comprise from about 0.11 to about 8 wt %, preferably from about 0.12 to about 6 wt %, more preferably from about 0.13 to about 4 wt %, still more preferably from about 0.14 to about 3 wt %, yet more preferably from about 0.15 to about 2 wt % and particularly from about 0.2 to about 1 wt % salicylic acid.

As a third essential ingredient, the inventive compositions comprise at least one compound of formula (I)

$$R_2\text{-}N(R_3)\text{-}CH(R_1)\text{-}(CH_2)_n\text{-}C(O)\text{-}OX \tag{I}$$

in which
n stands for 0 or 1,
X stands for —H, Na+, K+ or NH4+,
$R_1$ is selected from —H, —COOX or —($CH_2$)—COOX,
$R_2$ is selected from —H, $C_{1\text{-}10}$-alkyl or COOX,
$R_3$ is selected from —($CH_2$)—COOX, —($CH_2$)$_2$—N[($CH_2$)—COOX]$_2$, —CH($R_1$)—COOX, —($CH_2$)$_2$—NH[CH(COOX)($CH_2$COOX)], —CH($R_4$)—C($R_5$)($R_6$)—COOX
$R_4$ is selected from —H, $C_{1\text{-}10}$-alkyl or COOX,
$R_5$, $R_6$ are independently —H, —OH or $C_{1\text{-}10}$-alkyl.

Particularly preferred compounds of formula (I) are those in which n stands for 0 and $R_1$ for —H, so that formula (I) is simplified to formula (I-1):

$$R_2\text{-}N(R_3)\text{-}CH_2\text{-}C(O)\text{-}OX \tag{I-1}$$

in which
X stands for —H, Na+, K+ or NH4+,
$R_2$ is selected from —H, $C_{1\text{-}10}$-alkyl or COOX,
$R_3$ is selected from —($CH_2$)—COOX, —($CH_2$)$_2$—N[($CH_2$)—COOX]$_2$, —CH($R_1$)—COOX, —($CH_2$)$_2$—NH[CH(COOX)($CH_2$COOX)], —CH($R_4$)—C(RX)($R_6$)—COOX
$R_4$ is selected from —H, $C_{1\text{-}10}$-alkyl or COOX,
$R_5$, $R_6$ are independently —H, —OH or $C_{1\text{-}10}$-alkyl.

In a further preferred embodiment, $R_2$ in formula (I) stands for —($CH_2$)—COOX which simplifies formula to (I) to formula (I-2):

$$XO\text{-}C(O)\text{-}N(R_3)\text{-}CH(R_1)\text{-}(\,)_n\text{-}C(O)\text{-}OX \tag{I-2}$$

in which
n stands for 0 or 1,
X stands for —H, Na+, K+ or NH4+,
$R_1$ is selected from —H, —COOX or —($CH_2$)—COOX,
$R_3$ is selected from —($CH_2$)—COOX, —($CH_2$)$_2$—N[($CH_2$)—COOX]$_2$, —CH($R_1$)—COOX, —($CH_2$)$_2$—NH[CH(COOX)($CH_2$COOX)], —CH($R_4$)—C($R_5$)($R_6$)—COOX
$R_4$ is selected from —H, $C_{1\text{-}10}$-alkyl or COOX,
$R_5$, $R_6$ are independently —H, —OH or $C_{1\text{-}10}$-alkyl.

This preferred embodiment is also preferred for formula (I-1), is that formula (I-1) is simplified to formula (I-la):

$$XO\text{-}C(O)\text{-}CH_2\text{-}N(R_3)\text{-}CH_2\text{-}C(O)\text{-}OX \tag{I-1a}$$

in which
X stands for —H, Na+, K+ or NH4+,
$R_3$ is selected from —($CH_2$)—COOX, —($CH_2$)$_2$—N[($CH_2$)—COOX]$_2$, —CH($R_1$)—COOX, —($CH_2$)$_2$—NH[CH(COOX)($CH_2$COOX)], —CH($R_4$)—C($R_5$)($R_1$)—COOX $R_4$ is selected from —H, $C_{1-10}$-alkyl or COOX,
$R_5$, $R_6$ are independently —H, —OH or $C_{1-10}$-alkyl.

In a further preferred embodiment, $R_3$ in formula (I) stands for —$(CH_2)_2$—N[$(CH_2)$—COOX]$_2$, so that formula (I) is simplified to formula (I-3):

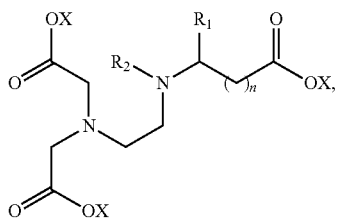

(I-3)

in which
n stands for 0 or 1,
X stands for —H, Na+, K+ or NH4+,
$R_1$ is selected from —H, —COOX or —$(CH_2)$—COOX,
$R_2$ is selected from —H, $C_{1-10}$-alkyl or COOX,
$R_4$ is selected from —H, $C_{1-10}$-alkyl or COOX,
$R_5$, $R_6$ are independently —H, —OH or $C_{1-10}$-alkyl.

This preferred embodiment is also preferred for formulas (I-1) and (I-2), so that formula (I-1) is simplified to formula (I-1b) and formula (I-2) is simplified to formula (I-2a):

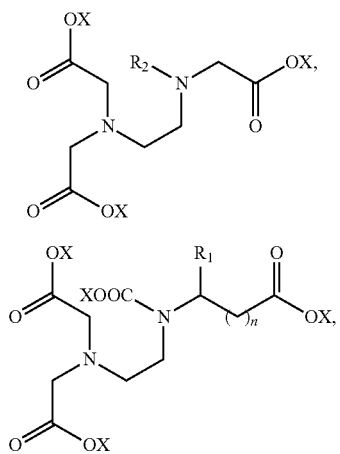

(I-1b)

(I-2a)

in which
n stands for 0 or 1,
X stands for —H, Na+, K+ or NH4+,
$R_1$ is selected from —H, —COOX or —$(CH_2)$—COOX,
$R_2$ is selected from —H, $C_{1-10}$-alkyl or COOX.

Particularly preferred are compounds with formula (I) in which n stands for 0, $R_1$ stands for —H, $R_2$ stands for —$(CH_2)$—COOX and $R_3$ stands for —$(CH_2)_2$—NH[$(CH_2)$—COOX]$_2$. Preferred antiperspirant cosmetic compositions as contemplated herein are therefore exemplified in that they comprise from about 0.012 to about 10 wt %, preferably from about 0.05 to about 5 wt %, more preferably from about 0.1 to about 2.5 wt %, still more preferably from about 0.15 to about 1 wt %, yet more preferably from about 0.2 to about 0.75 wt % and particularly from about 0.25 to about 0.5 wt % of compound(s) having formula (Ia)

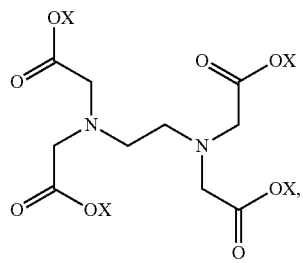

(Ia)

in which X stands for —H, Na+, K+, or NH4+.

In another, equally preferred embodiment, in formula (I) n stands for 0, $R_1$ stands for —H, $R_2$ stands for —$(CH_2)$—COOX and $R_3$ stands for —$(CH_2)$—COOX. Preferred antiperspirant cosmetic compositions as contemplated herein are therefore exemplified in that they comprise from about 0.012 to about 10 wt %, preferably from about 0.05 to about 5 wt %, more preferably from about 0.1 to about 2.5 wt %, still more preferably from about 0.15 to about 1 wt %, yet more preferably from about 0.2 to about 0.75 wt % and particularly from about 0.25 to about 0.5 wt % of compound(s) of formula (Ib)

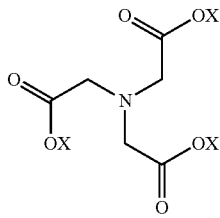

(Ib)

in which X stands for —H, Na+, K+ or NH4+.

In a similarly preferred embodiment, in formula (I) n stands for 0, $R_1$ stands for —$(CH_2)$—COOX, and $R_3$ stands for —CH($R_1$)—COOX. Antiperspirant cosmetic compositions preferred as contemplated herein are therefore exemplified in that they comprise from about 0.012 to about 10 wt %, preferably from about 0.05 to about 5 wt %, more preferably from about 0.1 to about 2.5 wt %, still more preferably from about 0.15 to about 1 wt %, yet more preferably from about 0.2 to about 0.75 wt %, and particularly from about 0.25 to about 0.5 wt % of compound(s) of formula (Ic)

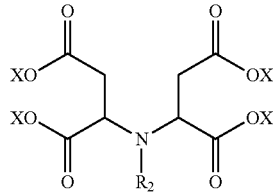

(Ic)

in which X stands for —H, Na+, K+ or NH4+ and $R_2$ is selected from —H or —$(CH_2)$—COOX.

Another group of preferred compounds of formula (I) is exemplified in that $R_3$ represents —$(CH_2)_2$—NH[CH(COOX)($CH_2$COOX)]. Preferred antiperspirant cosmetic compositions as contemplated herein are therefore exemplified in that they comprise from about 0.012 to about 10 wt %, preferably from about 0.05 to about 5 wt %, more preferably from about 0.1 to about 2.5 wt %, still more preferably from about 0.15 to about 1 wt %, yet more preferably from about 0.2 to about 0.75 wt % and particularly from about 0.25 to about 0.5 wt % of compound(s) having formula (Id)

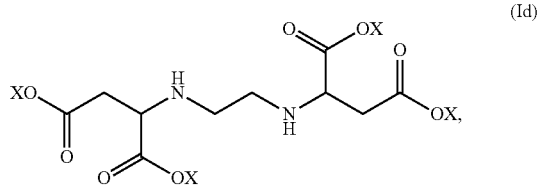

(Id)

in which X stands for —H, Na+, K+ or NH4+.

In all the formulas described in the preceding text, X can represent a hydrogen atom (free acid) or Na+, K+ or NH$_4$+. Partially neutralised forms in which X each is independently selected from the possibilities mentioned above and at least one X is —H are also usable as contemplated herein. Particularly preferred are the alkaline metal salts, including the sodium salts, that is to say those representatives in which each X stands for Na+.

A further group of preferred compounds of formula (I) is exemplified in that $R_3$ stands for —CH($R_4$)—C($R_5$)($R_6$)—COOX. Preferred antiperspirant cosmetic compositions as contemplated herein are therefore exemplified in that they comprise from about 0.012 to about 10 wt %, preferably from about 0.05 to about 5 wt %, more preferably from about 0.1 to about 2.5 wt %, still more preferably from about 0.15 to about 1 wt %, yet more preferably from about 0.2 to about 0.75 wt % and particularly from about 0.25 to about 0.5 wt % of compound(s) of formula (Ie)

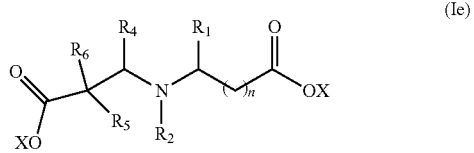

(Ie)

in which
n stands for 0 or 1,
X stands for —H, Na+, K+ or NH4+,
$R_1$ stands for —H or —(CH$_2$)—COOX,
$R_2$ is selected from —H or —(CH$_2$)—COOX,
$R_4$ is selected from —H, $C_{1-10}$-alkyl or COOX,
$R_5$, $R_6$ are independently —H, —OH or $C_{1-10}$-alkyl.

As used herein, "alkyl" refers to saturated straight or branched chain hydrocarbons having 1-10, preferably 1-4 carbon atoms and includes but is not limited to methyl, ethyl, n-propyl, isopropyl, n-butyl, sec-butyl, isobutyl and tert-butyl.

Particularly preferred antiperspirant cosmetic compositions of this embodiment are exemplified in that the compound(s) of formula (Id) is/are selected from the group of N-(1,2-dicarboxy-2-hydroxyethyl) glycine, N-(1,2-dicarboxy-2-hydroxyethyl) alanine, N,N-biscarboxymethyl-3-alanine, N-(1,2-dicarboxy-2-hydroxyethyl) sarcosine, N-(1,2-dicarboxy-2-hydroxyethyl) iminodiacetic acid and the alkaline metal salts, especially the Na salts thereof.

As contemplated herein, it is further preferred if the antiperspirant cosmetic composition further comprises at least one preservative. Preferred preservatives as contemplated herein are formaldehyde releasing agents iodopropinylbutyl carbamates, parabenes, phenoxyethanol, ethanol, benzoic acid and salts thereof, dibromodicyanobutane, 2-bromo-2-nitro-propane-1,3-diol, imidazolidinyl urea, 5-chloro-2-methyl-4-isothiazolin-3-one, 2-chloroacetamide, benzalkonium chloride, benzyl alcohol. Other preservatives that are usable within the scope of the present disclosure are the substances listed in Annex 6 of the Cosmetics Ordinance and cosmetic raw materials with preservative properties or raw materials which support or enhance the preservative effect of the aforementioned preservatives. The preservatives are preferably included in a total quantity of about 0.01 to about 10 wt %, preferably from about 0.1 to about 7 wt %, more preferably from about 0.2 to about 5 wt %, particularly from about 0.3 to about 2.0 wt % relative to the total weight of the antiperspirant cosmetic composition.

Within the scope of the present disclosure, it is preferable that the antiperspirant cosmetic agent is present as a water-in-oil emulsion. This may in particular be a sprayable water-in-oil emulsion, which can be sprayed using a propellant.

However, it may be equally preferred as contemplated herein if the antiperspirant cosmetic is an oil-in-water. In this case, the inventive cosmetic agent is preferably sprayed as a propellant-free pump spray or squeeze spray or applied as a roll-on.

According to another preferred embodiment of the present disclosure, the cosmetic compositions as contemplated herein may comprise only a small amount of free water or no free water. For the purposes of the present disclosure, free water is understood to be water that differs from crystallisation water, hydration water or similarly molecularly bound water of the constituents. The antiperspirant cosmetic agent preferably comprises free water in a total quantity less than about 10 wt %, preferably less than about 8 wt %, more preferably less than about 5 wt %, still more preferably less than about 3 wt %, yet more preferably less than about 1 wt %, particularly about 0 wt %, relative to the total weight of the antiperspirant cosmetic product.

A part of another embodiment, however, it is also preferred as contemplated herein if the antiperspirant cosmetic composition is an aqueous, aqueous-alcoholic or aqueous-glycolic solution.

In the context of this variant of the present disclosure, surprisingly it was found that the antiperspirant effect can be enhanced significantly if the inventive antiperspirant cosmetic compositions comprise free water in a quantity from about 5 to about 99 wt % relative to the total weight of the antiperspirant cosmetic agent. In a particularly preferred embodiment of the present disclosure, the antiperspirant cosmetic composition therefore comprises free water in a total amount from about 5 to about 96 wt %, preferably from about 15 to about 80 wt %, more preferably from about 30 to about 70 wt %, particularly from about 40 to about 60 wt % relative to the total weight of the antiperspirant cosmetic product.

In the context of this embodiment, it is further preferred if the antiperspirant cosmetic comprises ethanol in a total amount from about 1 to about 99 wt %, preferably from about 5 to about 70 wt %, more preferably from about 7 to about 50 wt %, particularly from about 10 to about 30 wt %, relative to the total weight of the antiperspirant cosmetic product. The antiperspirant cosmetic composition as contemplated herein can be applied by various methods.

According to a preferred embodiment, the antiperspirant cosmetic composition is packaged for spray application. The spray application is carried out with a spray device which comprises a quantity of the inventive antiperspirant cosmetic agent in a container in liquid, viscous-flowable, suspension or powdered form. The included quantity may be under pressure from a propellant (pressurised gas cans, pressurised gas dispensers, aerosol dispensers), or it may be a mechanically operated pump atomiser without propellant gas (pump sprays/squeeze bottle). In this context, the antiperspirant cosmetic composition may be atomised physically, mechanically or electromechanically, for example by piezoeffects or electric pumps.

The antiperspirant cosmetic product may further preferably be prepared in the form of a pencil, soft solid, cream, gel, roll-on, loose or compact powder. The formulation of the antiperspirant cosmetic compositions as contemplated herein in a particular application form, such as an antiperspirant roll-on, an antiperspirant pencil or an antiperspirant gel is preferably adapted to meet the requirements of the intended use. Depending on their intended use, the antiperspirant cosmetic products of the present disclosure may therefore be in solid, semi-solid, liquid, dispersed, emulsified, suspended, gel, multi-phase or powdered form. The notion of liquid within the meaning of the present disclosure also encompasses all types of solid dispersions in liquids. Moreover, for the purposes of the present disclosure, multiphase antiperspirant cosmetic products as contemplated herein are understood to be those which have at least 2 different phases with phase separation and in which the phases may be located horizontal, that is one on top of the other, or vertically, that is to say side by side. They may be applied, for example with a roll-on ball applicator or by means of a solid stick.

Within the scope of the present disclosure it may also be preferred if the antiperspirant cosmetic is included on and/or in a disposable substrate selected from the group of wipes, pads, and swabs. Particularly preferred are wet wipes, i.e. wipe that have been prefabricated and preferably packaged individually for the user, disposable cloths, such as are well known from the field of glass cleaning or wet toilet paper, for example. Such wet wipes, which may advantageously also comprise preservatives, are impregnated or charged with an antiperspirant cosmetic product as contemplated herein and preferably packaged individually. Preferred substrate materials are selected from porous flat cloths. Such cloths include cloths made of woven and nonwoven synthetic and natural fibres, felt, paper or foam, such as hydrophilic polyurethane foam. Preferred deodorant or antiperspirant substrates as contemplated herein may be prepared by soaking or impregnating or melting an antiperspirant cosmetic composition of the present disclosure onto a substrate.

As contemplated herein, the antiperspirant cosmetic product preferably comprises at least one further adjuvant selected from the group of (i) emulsifiers and/or surfactants; (ii) thickening agents, (iii) active deodorants; (iv) mono- and/or polyvalent alcohols and/or polyethylene glycols; (v) skin-cooling active ingredients; (vi) pH adjusters; (vii) skin conditioners such as moisturisers, skin soothing agents, skin lightening agents, skin smoothing substances; and (viii) mixtures thereof.

Preferred emulsifiers and surfactants as contemplated herein are selected from anionic, cationic, nonionic, amphoteric, especially ampholytic and zwitterionic emulsifiers and surfactants. Surfactants are amphiphilic (bifunctional) compounds which comprise at least one hydrophobic and at least one hydrophilic moiety. The hydrophobic radical is preferably a hydrocarbon chain having 8 to 28 carbon atoms which may be saturated or unsaturated, linear or branched. Particularly preferably, this $C_8$-$C_{28}$ alkyl chain is linear.

In order to thicken the antiperspirant cosmetic compositions as contemplated herein, substances are preferably used which are selected from cellulose ethers, xanthan gum, *sclerotium* gum, succinoglucanes, polygalactomannans, pectins, agar, carrageenan, tragacanth, gum arabic, karaya gum, tara gum, gellan, gelatin, propylene glycol alginate, alginic acids and salts thereof, polyvinyl pyrrolidones, polyvinyl alcohols, polyacrylamides, physically (for example, by pregelatinization) and/or chemically modified starches, acrylic acid-acrylate copolymers, acrylic acid-acrylamide copolymers, acrylic acid-vinylpyrrolidone copolymers, acrylic acid-vinyl formamide copolymers and polyacrylates. Particularly preferred thickeners are also selected from carbomers. Carbomers are thickening crosslinked polymers of acrylic acid, methacrylic acid and their salts. Crosslinking can be effected by means of polyfunctional compounds such as polyalkylene ethers of polysaccharides or polyalcohols, for example sucrose allyl ether, pentaerythritol allyl ether, propylene allyl ether. Preferred in the context of the present disclosure are homopolymers of acrylic acid or salts thereof, which are crosslinked with a pentaerythritol allyl ether, a sucrose allyl ether or a propylene allyl ether. One thickener that is usable for the purposes of the present disclosure is a copolymer of $C_{10\text{-}30}$-alkyl acrylate, acrylic acid, methacrylic acid and esters thereof, which is crosslinked with a sucrose allyl ether or pentaerythritol allyl ether. Thickeners based on carbomers are marketed under the trade name Carbopol® (BF Goodrich, Ohio, USA) and include products such as Carbopol 934, Carbopol 940, Carbopol 941, Carbopol 971, Carbopol 974, Carbopol EZ2, Carbopol ETD 2001, Carbopol ETD 2020 Carbopol ETD 2050, Carbopol Ultrez 10, Carbopol Ultrez 20, or Carbopol Ultrez 21.

Lipophilic thickeners may also be used to thicken the inventive antiperspirant cosmetic compositions. Preferred lipophilic thickeners as contemplated herein are selected from hydrophobicised clay minerals, bentonites, fumed silicas and their derivatives.

The deodorising effect of the antiperspirant cosmetic compositions as contemplated herein may be enhanced further if at least one active deodorant agent with antibacterial and/or bacteriostatic and/or enzyme inhibiting and/or odour-neutralising and/or odour-absorbing effect is included in a total amount from about 0.0001 to about 40 wt %, preferably from about 0.2 to about 20 wt %, more preferably from about 1 to about 15 wt %, particularly from about 1.5 to about 5 wt % relative to the total weight of the antiperspirant cosmetic composition. If ethanol is used in the compositions as contemplated herein, within the scope of the present disclosure it is considered not as an active deodorant ingredient but as a component of the carrier.

Preferred inventive antiperspirant cosmetic compositions further comprise at least one water-soluble polyvalent $C_{2\text{-}9}$-alkanol with about 2 to about 6 hydroxyl groups and/or at least one water-soluble polyethylene glycol with about 3 to about 50 ethylene oxide units and mixtures thereof. These do not include the active deodorant agents in the form of 1,2-alkanediols mentioned previously.

According to a further embodiment of the present disclosure, the antiperspirant cosmetic products also comprise at least one skin-cooling active substance. Skin-cooling active ingredients that are suitable as contemplated herein are for example menthol, isopulegol and menthol derivatives, e.g., menthyl lactate, menthyl glycolate, menthyl ethyl oxamate, menthylpyrrolidone carboxylic acid, menthyl methyl ether, menthoxypropanediol, menthone glycerine acetol (9-methyl-6-(1-methylethyl)-1,4-dioxaspiro (4,5)decane-2-methanol), monoethnyl succinate, 2-hydroxymethyl-3,5, 5-trimethylcyclohexanol and 5-methyl-2-(1-methylethyl)cyclohexyl-N-ethyl oxamate. Preferred skin-cooling active substances are menthol, isopulegol, menthyl lactate, menthoxypropanediol, menthylpyrrolidone carboxylic acid and 5-methyl-2-(1-methylethyl)cyclohexyl-N-ethyl oxamate and mixtures of these substances, particularly mixtures of menthol and menthyl lactate, menthol, menthol glycolate and menthyl lactate, menthol and menthoxypropanediol or menthol and isopulegol.

The pH adjusters that are preferably used as contemplated herein are acids and/or alkalising agents and/or buffers. Preferred acid substances used as contemplated herein include inorganic acids (such as hydrochloric, sulphuric or phosphoric acid) or organic acids (such as citric acid, tartaric acid or malic acid). The alkalising agents usable as contemplated herein are preferably selected from the group of ammonia, basic amino acids, alkaline hydroxides, carbonates and bicarbonates, alkanolamines, for example, amino-2-methyl-1-propanol, monoethanolamine, triethanolamine, diethanolamine, and triisopropanolamine, alkaline metal metasilicates, urea, morpholine, N-methylglucamine, imidazole, alkaline phosphates and alkaline hydrogen phosphates. The alkaline metal ions used for preference are those of lithium, sodium, potassium, particularly sodium or potassium. Buffer systems that are suitable within the scope of the present disclosure include in particular carbonic acid bicarbonate buffer, carbonic acid silicate buffer, acetic acid acetate buffer, phosphate buffer, ammonia buffer, citric acid or citrate buffer based on tris(hydroxymethyl)-aminomethane, buffers based on 4-(2-hydroxyethyl)-1-piperazine ethane sulphonic acid, buffers based on 4-(2-hydroxyethyl) piperazine-1-propanesulphonic acid, buffers based on 2-(N-morpholino)ethanesulphonic acid, and barbital acetate buffers. In this context, the choice of appropriate buffer system depends on the desired pH of the antiperspirant cosmetic compositions as contemplated herein.

Within the scope of the present disclosure, it may also be provided to prepare the inventive cosmetic products as a two-component agent. For this purpose, the individual components are preferably stored in separate containers and applied to the skin sequentially in any order or simultaneously. Separation into multicomponent systems is particularly preferred where it is expected or feared that the skin may present intolerances towards the ingredients.

Another object of the present disclosure is therefore a packaging unit (kit-of-parts) comprising—packaged separately from one another— a) at least a first container (C1) comprising a cosmetic product (M1) comprising at least one antiperspirant compound, and b) at least a second container (C2) comprising a cosmetic product (M2) comprising at least salicylic acid and at least one compound of formula (I), wherein the cosmetic product (M2) comprises no antiperspirant compound.

In the context of the present disclosure, the term "antiperspirant compound" is understood to encompass the abovementioned halides and/or hydroxyhalides of aluminium and/or zirconium, compounds of the formulas $Al(OH)_yX$ and $Zr(OH)_zX$, wherein X in the abovementioned formulas stands for a halide ion, and complexes of halides and/or hydroxyhalides of aluminium and/or zirconium with ligands, such as amino acids, betaines and hydroxyalkanoic acids.

The previous notes regarding cosmetic product products as contemplated herein apply both to the cosmetic product (M1) in container (C1) and mutatis mutandis to the cosmetic product (M2) in container (C2).

Finally, a further object of the present disclosure is a non-therapeutic cosmetic method for preventing and/or reducing the body perspiration, in which an antiperspirant cosmetic composition as contemplated herein or the content of a packaging unit as contemplated herein is applied to the skin, particularly to the skin of armpits, and remains in place for at least about 1 hour, preferably at least about 2 hours, more preferably at least about 4 hours, most preferably at least about 6 hours.

If the inventive packaging unit is used as part of the method as contemplated herein, it may be provided that the cosmetic product (M1) in container (C1) is applied first, followed by the cosmetic agent (M2) in container (C2). However, it is also possible for the cosmetic composition (M2) in container (C2) to be applied first, and then the cosmetic product (M1) in container (C1). In addition, cosmetic product (M1) in container (C1) and the cosmetic product (M2) in container (C2) may also be applied at the same time. The time interval between applications of the two compositions (M1) and (M2) is from about 0 seconds to about 24 hours.

The preceding notes regarding the inventive method may also apply mutatis mutandis with regard to the antiperspirant cosmetic products a as contemplated herein and the use as contemplated herein.

Examples

1. Antiperspirant Roll-On—Emulsions

|  | 1.1 wt % | 1.2 wt % | 1.3 wt % | 1.4 wt % |
|---|---|---|---|---|
| PPG-15 stearyl ether | 0.5 | 0.5 | 0.5 | 0.5 |
| Steareth-2 | 2.5 | 2.5 | 2.5 | 2.5 |
| Steareth-21 | 1.0 | 1.0 | 1.0 | 1.0 |
| Cetearyl alcohol (Lanette O, BASF) | 0.5 | 0.5 | — | 0.5 |
| Dimethicone (Xiameter PMX-200 Sil Fluid 5CS) | 3% | 3% | — | 3% |
| Salicylic acid | 0.5% | 0.5% | 0.5% | 0.5% |
| Aluminium sesquichlorohydrate (Reach 301 L, 40% in water) | 25.0 | — | — | — |
| Aluminium chlorohydrate (Locron L from Clariant, 50% in water) | — | 27.0 | 27.0 | — |
| Aluminium zirconium tetrachlorohydrex (AZG 364 from Summit Reheis) | — | — | — | 23.0 |
| EDTA BX Powder (BASF) | 0.1 | 0.1 | 0.1 | 0.1 |
| Fragrance | 1.0 | 1.0 | 1.0 | 1.0 |
| Water | To 100 | To 100 | To 100 | To 100 |

2. Antiperspirant Roll-On—Alcoholic Solutions

|  | 2.1 wt % | 2.2 wt % | 2.3 wt % | 2.4 wt % |
|---|---|---|---|---|
| Ethanol (96% solution) | 30.0 | 30.0 | 30.0 | 30.0 |
| Hydroxyethylcellulose (Tylose H) | 0.4 | 0.4 | 0.4 | 0.4 |
| Cetaereth-12 (Emulgin B1, BASF) | 2.0 | 2.0 | 2.0 | 2.0 |
| Cetaereth-30 (Emulgin B3, BASF) | 2.0 | 2.0 | 2.0 | 2.0 |
| Salicylic acid | 0.5% | 0.5% | 0.5% | 0.5% |
| Aluminium chlorohydrate (Locron L from Clariant, 50% in water) | 16.0 | 40.0 | 16.0 | — |

-continued

|  | 2.1 wt % | 2.2 wt % | 2.3 wt % | 2.4 wt % |
| --- | --- | --- | --- | --- |
| Aluminium zirconium tetrachlorohydrex (AZG 364 from Summit Reheis) | — | — | — | 23.0 |
| EDTA BX Powder (BASF) | 0.1 | 0.1 | 0.1 | 0.1 |
| Fragrance | 1.0 | 1.0 | 1.0 | 1.0 |
| Water | To 100 | To 100 | To 100 | To 100 |

3. Antiperspirant Aerosol

|  | 3.1 wt % | 3.2 wt % | 3.3 wt % |
| --- | --- | --- | --- |
| Cyclopentasiloxane (Xiameter PMX-0245) | 10.7 | 10.7 | 10.7 |
| Dow Corning ES-5227 DM[1] | 5.6 | 5.6 | 5.6 |
| Isopropyl myristate (BASF) | 6.6 | 6.6 | 6.6 |
| Propylene glycol | 23.4 | 23.4 | 23.4 |
| Phenoxyethanol | 0.5 | 0.5 | 0.5 |
| Aluminium sesquichlorohydrate (Reach 301 L, 40% in water) | 20.0 | 25.0 | 30.0 |
| Aluminium chlorohydrate (Locron L from Clariant, 50% in water) | — | 27.0 | 27.0 |
| Salicylic acid |  |  |  |
| EDTA BX Powder (BASF) | 0.05 | 0.1 | 0.15 |
| Fragrance | 2.5 | 2.5 | 2.5 |
| Water | 29.7 | 24.7 | 18.7 |

[1]25% PEG/PPG-18/18 Dimethicone/85% Dimethicone 5 cts

Recipes 3.1, 3.2 und 3.3 filled into aerosol cans with the propellant gas propane/butane (15/85) in a weight ratio of 1:4.

4. Clear Gel

|  | 4.1 | 4.2 | 4.3 |
| --- | --- | --- | --- |
| Aluminium chlorohydrate (Locron L from Clariant, 50% in water) | 32.832.8 | 32.8 | 32.8 |
| Ethanol (96% solution) | 11.0 | 11.0 | 11.0 |
| Xiameter PMX-2147 Fluid | 7.0 | 7.0 | 7.0 |
| Dow Corning 5225 Formulation Aid | 9.0 | 9.0 | 9.0 |
| Propylene glycol | 6.0 | 6.0 | 6.0 |
| Salicylic acid | 0.2 | 0.5 | 1.0 |
| EDTA BX Powder (BASF) | 0.05 | 0.1 | 0.15 |
| Fragrance | 0.5 | 0.5 | 0.5 |
| Water | To 100 | To 100 | To 100 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An antiperspirant cosmetic composition comprising, relative to the total weight of the antiperspirant cosmetic composition,
   a) from about 1 to about 30 wt % of at least one antiperspirant compound,
   b) from about 0.1 to about 10 wt % salicylic acid, and
   c) at least one compound with formula (I)

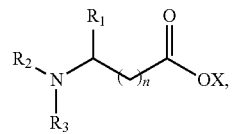

in which
n stands for 0 or 1,
X stands for —H, Na$^+$, K$^+$ or NH4$^+$,
R$_1$ is selected from —H, —COOX or —(CH$_2$)—COOX,
R$_2$ is selected from —H, C$_{1\text{-}10}$-alkyl or COOX,
R$_3$ is selected from —(CH$_2$)—COOX, —(CH$_2$)$_2$—N[(CH$_2$)—COOX]$_2$, —CH(R$_1$)—COOX, —(CH$_2$)$_2$—NH[CH(COOX)(CH$_2$COOX)], or —CH(R$_4$)—C(R$_5$)(R$_6$)—COOX,
R$_4$ is selected from —H, C$_{1\text{-}10}$-alkyl or COOX, and
R$_5$ and R$_6$ are independently —H, —OH or C$_{1\text{-}10}$-alkyl.

2. The antiperspirant cosmetic composition according to claim 1, comprising from about 2 to about 25 wt % aluminium chlorohydrate.

3. The antiperspirant cosmetic composition according to claim 1, comprising from about 2.5 to about 29 wt % aluminium-zirconium chlorohydrate.

4. The antiperspirant cosmetic composition according to claim 1, comprising from about 0.11 to about 8 wt % salicylic acid.

5. The antiperspirant cosmetic composition according to claim 1, comprising from about 0.012 to about 10 wt % of compound(s) of formula (Ia)

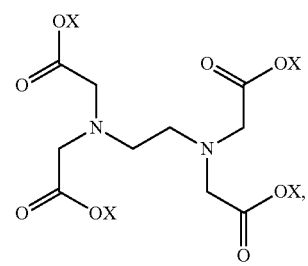

in which
X stands for —H, Na$^+$, K$^+$, or NH4$^+$.

6. The antiperspirant cosmetic composition according claim 1, comprising from about 0.012 to about 10 wt % of compound(s) of formula (Ib)

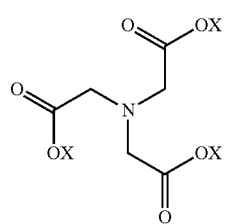

in which

X stands for —H, Na⁺, K⁺ or NH4⁺.

7. The antiperspirant cosmetic composition according claim 1, comprising from about 0.012 to about 10 wt % of compound(s) of formula (Ic)

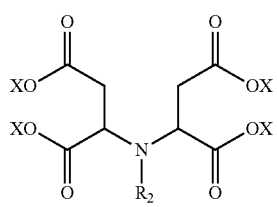

(Ic)

in which

X stands for —H, Na+, K+ or NH4+ and
R₂ is selected from —H or —(CH₂)—COOX.

8. The antiperspirant cosmetic composition according claim 1, comprising from about 0.012 to about 10 wt % of compound(s) having formula (Id)

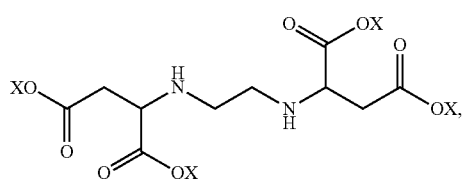

(Id)

in which

X stands for —H, Na+, K+ or NH4+.

9. The antiperspirant cosmetic composition according to claim 1, comprising from about 0.012 to about 10 wt % of compound(s) of formula (Ie)

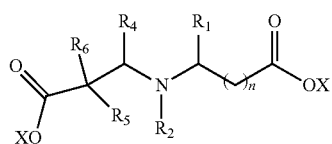

(Ie)

in which n stands for 0 or 1,
X stands for —H, Na⁺, K⁺ or NH4⁺,
R₁ stands for —H or —(CH₂)—COOX,
R₂ is selected from —H, $C_{1-10}$-alkyl or COOX,
R₄ is selected from —H, $C_{1-10}$-alkyl or COOX, and
R₅ and R₆ are independently —H, —OH or $C_{1-10}$-alkyl.

10. The antiperspirant cosmetic composition according to claim 8, wherein the compound(s) of formula (Id) is selected from the group of N-(1,2-dicarboxy-2-hydroxyethyl) glycine, N-(1,2-dicarboxy-2-hydroxyethyl) alanine, N,N-bis-carboxymethyl-β-alanine, N-(1,2-dicarboxy-2-hydroxyethyl) sarcosine, N-(1,2-dicarboxy-2-hydroxyethyl) iminodiacetic acid and the alkaline metal salts.

11. A non-therapeutic cosmetic method for preventing and/or reducing body perspiration comprising applying the antiperspirant cosmetic composition according to claim 1 to skin, wherein the antiperspirant cosmetic composition remains in contact with the skin for at least about 1 hour.

12. The antiperspirant cosmetic composition according to claim 1, comprising from about 3 to about 24 wt % aluminium chlorohydrate.

13. The antiperspirant cosmetic composition according to claim 1, comprising from about 5 to about 28 wt % aluminium-zirconium chlorohydrate.

14. The antiperspirant cosmetic composition according to claim 1, comprising from about 0.12 to about 6 wt % salicylic acid.

15. The antiperspirant cosmetic composition according to claim 1, comprising from about 0.05 to about 5 wt % of compound(s) of formula (Ia)

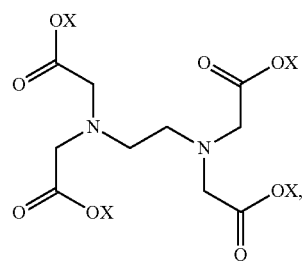

(Ia)

in which

X stands for —H, Na⁺, K⁺, or NH4⁺.

16. The antiperspirant cosmetic composition according to claim 1, comprising from about 0.05 to about 5 wt % of compound(s) of formula (Ib)

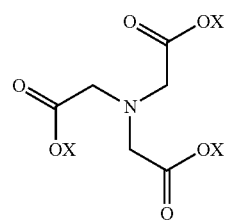

(Ib)

in which

X stands for —H, Na⁺, K⁺ or NH4⁺.

17. The antiperspirant cosmetic composition according to claim 1, comprising from about 0.05 to about 5 wt % of compound(s) of formula (Ic)

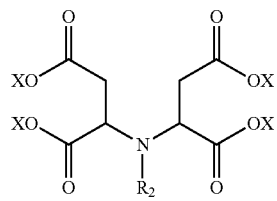

(Ic)

in which

X stands for —H, Na+, K+ or NH4+ and
R₂ is selected from —H or —(CH₂)—COOX.

18. The antiperspirant cosmetic composition according to claim 1, comprising from about 0.05 to about 5 wt % of compound(s) having formula (Id)

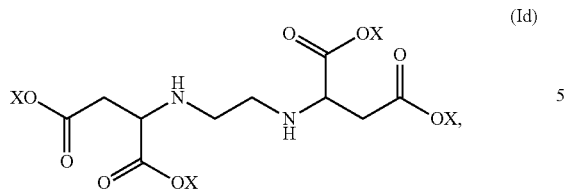
(Id)

in which
X stands for —H, Na+, K+ or NH4+.

19. The antiperspirant cosmetic composition according to claim 1, comprising from about 0.05 to about 5 wt % of compound(s) of formula (Ie)

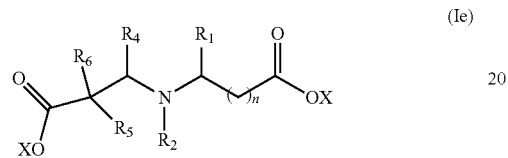
(Ie)

in which
n stands for 0 or 1,
X stands for —H, $Na^+$, $K^+$ or $NH4^+$,
$R_1$ stands for —H or —$(CH_2)$—COOX,
$R_2$ is selected from —H, $C_{1-10}$-alkyl or COOX,
$R_4$ is selected from —H, $C_{1-10}$-alkyl or COOX, and
$R_5$ and $R_6$ are independently —H, —OH or $C_{1-10}$-alkyl.

\* \* \* \* \*